(12) United States Patent
Park

(10) Patent No.: US 12,127,914 B2
(45) Date of Patent: Oct. 29, 2024

(54) MEDICAL DRESSING PATCH AND MANUFACTURING METHOD THEREOF

(71) Applicant: Young Joon Park, Yangsan-si (KR)

(72) Inventor: Young Joon Park, Yangsan-si (KR)

(73) Assignee: Young Joon Park (KR)

( * ) Notice: Subject to any disclaimer, the term of this patent is extended or adjusted under 35 U.S.C. 154(b) by 368 days.

(21) Appl. No.: 17/687,876

(22) Filed: Mar. 7, 2022

(65) Prior Publication Data

US 2022/0183898 A1    Jun. 16, 2022

Related U.S. Application Data

(63) Continuation of application No. PCT/KR2019/014705, filed on Nov. 1, 2019.

(30) Foreign Application Priority Data

Sep. 25, 2019    (KR) .......................... 10-2019-0117963

(51) Int. Cl.
*A61F 13/00*    (2024.01)
*A61F 13/02*    (2006.01)
*A61F 13/0246*    (2024.01)

(52) U.S. Cl.
CPC ...... *A61F 13/0259* (2013.01); *A61F 13/0246* (2013.01); *A61F 13/0289* (2013.01);
(Continued)

(58) Field of Classification Search
None
See application file for complete search history.

(56) References Cited

U.S. PATENT DOCUMENTS 6,140,549 A * 10/2000 Pompei, Jr. ........... A61F 15/001
602/41
2018/0243141 A1    8/2018 Park

FOREIGN PATENT DOCUMENTS

KR    200439156 Y1    3/2008
KR    101248121 B1    4/2013
(Continued)

OTHER PUBLICATIONS

KR 101842697 B1 Translation (Year: 2018).*
(Continued)

*Primary Examiner* — Kim M Lewis
(74) *Attorney, Agent, or Firm* — Park & Associates IP Law Office

(57) ABSTRACT

A medical dressing includes: a lower support film; a release film; and an adhesive sheet part (110) for application, which is placed on the release film (200) and is attached to the skin, wherein the release film (200) consists of a release film part (210) for fixing and a separable release film part (220) to be separated therefrom by a cutting line (211) formed on the release film part (210) for fixing, so that a predetermined region of the separable release film part is positioned to overlap with the bottom surface of the adhesive sheet part (110), thereby allowing, during separation of the separable release film part (220) from the release film part (210) for fixing, separation together with the adhesive sheet part (110) for application, and the area of the separable release film part (220), which overlaps with the bottom surface of the adhesive sheet part (110), is relatively smaller than the area of the separable release film part, which does not overlap with the adhesive sheet part (110).

10 Claims, 9 Drawing Sheets

(52) U.S. Cl.
CPC .............. *A61F 2013/008* (2013.01); *A61F 2013/00817* (2013.01)

(56) References Cited

FOREIGN PATENT DOCUMENTS

| | | | |
|---|---|---|---|
| KR | 101624562 | B1 | 5/2016 |
| KR | 2020160002587 | U | 7/2016 |
| KR | 101736212 | B1 | 5/2017 |
| KR | 101842697 | B1 * | 3/2018 |
| KR | 1020180110397 | A | 10/2018 |
| KR | 1020180117865 | A | 10/2018 |
| KR | 1020180118080 | A | 10/2018 |
| KR | 101934882 | B1 | 1/2019 |

OTHER PUBLICATIONS

KR2016-0002587 U Translation (Year: 2016).*
Korean Office Action (KR 10-2019-0117963), KIPO, 2019-10-18.
Korean Notice of Allowance (KR 10-2019-0117963), KIPO, 2019-12-10.
International Search Report (PCT/KR2019/014705), WIPO, Jun. 23, 2020.
Taiwan Office Action (TW 109121598), TIPO, Jan. 13, 2021.

* cited by examiner

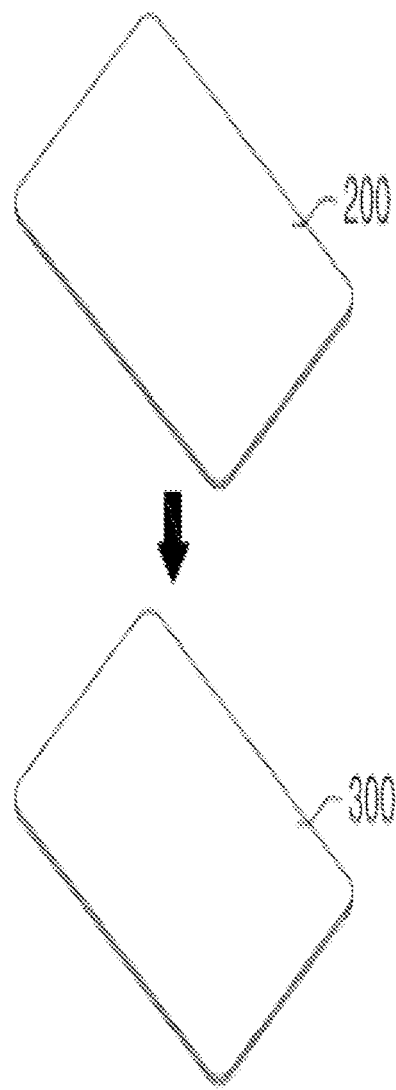
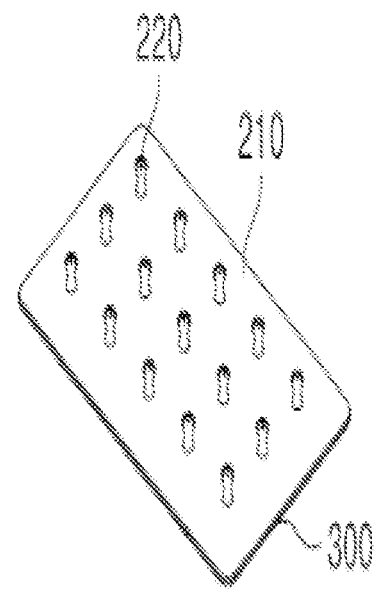
FIG. 4A
FIG. 4B

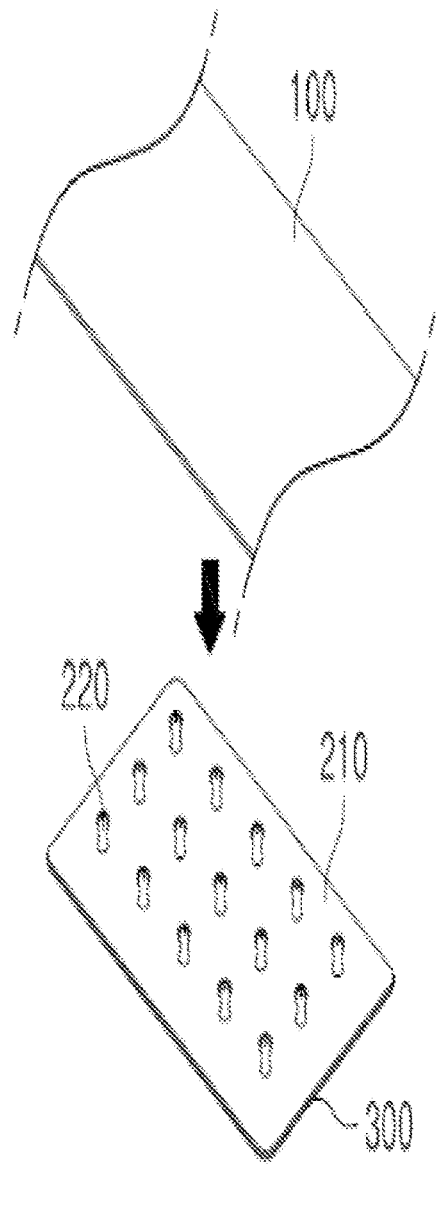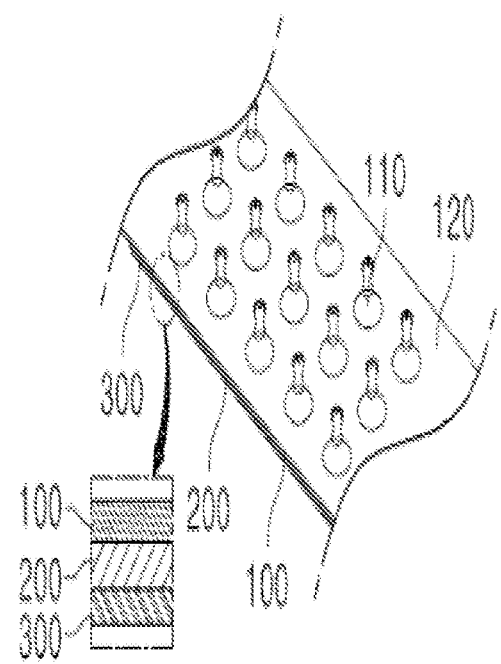
FIG. 4C
FIG. 4D

MEDICAL DRESSING PATCH AND MANUFACTURING METHOD THEREOF

REFERENCE TO RELATED APPLICATIONS

This is a continuation of International Patent Application PCT/KR2019/014705 filed on Nov. 1, 2019, which designates the United States and claims priority of Korean Patent Application No. 10-2019-0117963 filed on Sep. 25, 2019, the entire contents of which are incorporated herein by reference.

FIELD OF THE INVENTION

The present invention relates to a medical dressing used to treat a wound on the skin, such as a burn, a cut, or a trauma, while protecting the wound and a method of manufacturing the same, and more particularly to a medical dressing including an adhesive sheet portion for application configured to be attached to the skin, a separable release film portion configured to separate the adhesive sheet portion for application so as to be attached to the skin, and a lower support film disposed thereunder, whereby convenience in use and storability thereof are improved, and a method of manufacturing the same.

BACKGROUND OF THE INVENTION

In general, a medical dressing is widely used to treat a wound on the skin, such as a minor burn, a cut, or a trauma, while protecting the wound. That is, the medical dressing provides a function of reducing thermal evaporation and moisture loss from the surface of the wound to prevent further contamination and a function of reducing growth of bacteria in the wound.

The medical dressing is configured such that an adhesive sheet is attached to an upper surface of release paper. The adhesive sheet is separated from the release paper, and an attachment surface formed at a lower surface of the adhesive sheet is attached to the wound, whereby the above functions are provided.

In order to separate the adhesive sheet from the release paper, the adhesive sheet is separated from the release paper while holding one side of the adhesive sheet, and then the adhesive sheet is attached to the wound. During this process, however, a user holds the adhesive sheet, whereby contamination may occur. In addition, since the thickness of the adhesive sheet has been gradually decreased in order to further guarantee wearing sensation and activity of a patient to whom the adhesive sheet is attached, separation of the adhesive sheet from the release paper is also inconvenient, whereby convenience in use is lowered.

Meanwhile, in recent years, demand for a hydrocolloid adhesive sheet having excellent wound protection ability and adhesive force has increased. Since the hydrocolloid adhesive sheet is thin and transparent, it is difficult to recognize the hydrocolloid adhesive sheet with the naked eye when the hydrocolloid adhesive sheet is attached to the skin, in addition to wearing sensation and activity of the patient, whereby the hydrocolloid adhesive sheet is advantageous in terms of aesthetics. However, it is very difficult to separate the hydrocolloid adhesive sheet from the release paper due to transparent and thin characteristics thereof.

Korean Registered Utility Model Publication No. 439156 is disclosed as prior art for solving the above problem. In the disclosure of this prior art, a protective sheet is easily separated from separable release paper while holding a grip portion of the release paper, the protective sheet is attached to a wound, and the separable release paper is separated from the protective sheet.

In the above construction, the protective sheet is separated from the separable release paper while holding the grip portion of the separable release paper, not holding the protective sheet, and is attached to the wound, whereby it is possible to obtain an effect of preventing secondary bacterial infection while achieving convenience.

Since the area of the grip portion is small and an attachment surface of the portion of the separable release paper that is attached to the protective sheet is wide, however, it is very inconvenient to hold the grip portion by hand. In addition, when the protective sheet is separated from the separable release paper while holding the grip portion, a phenomenon in which the grip portion is separated frequently occurs. In order to prevent this, the portion of the separable release paper that is attached to the surface of the protective sheet must be very carefully separated while holding the grip portion, and therefore a lot of time is incurred from separation to attachment to the wound. Furthermore, the hand of the user may come into contact with an adhesive portion of the protective sheet during this process, whereby secondary bacterial infection may be caused.

In order to remedy the above problems, the applicant of the present application has applied for a patent on a medical dressing including separable release paper, configured to be fixed to or separated from fixed release paper by an incision portion and a connection portion formed at the fixed release paper, and an adhesive located so as to partially overlap the separable release paper, thereby preventing secondary bacterial infection while improving convenience in use (10-2017-0020663), which has been registered as a patent.

PRIOR ART DOCUMENTS

Patent Documents

Korean Registered Utility Model Publication No. 439156
Korean Patent Application No. 2017-0020663

SUMMARY OF THE INVENTION

The present invention is an improvement to the invention of a prior application filed by the applicant of the present application, and it is an object of the present invention to provide a medical dressing capable of fundamentally preventing separation of only a separable release film portion and preventing damage to an adhesive sheet portion for application and a method of manufacturing the same.

A medical dressing according to the present invention includes a release film (200) and an adhesive sheet portion (110) for application located on the release film (200), the adhesive sheet portion being configured to be attached to the skin, wherein the release film (200) is constituted by a fixed release film portion (210) and a separable release film portion (220) configured to be separated along an incision line (211) formed in the fixed release film portion (210), a predetermined region of the separable release film portion (220) overlapping a lower surface of the adhesive sheet portion (110) for application such that the separable release film portion is separated together with the adhesive sheet portion (110) for application when being separated from the fixed release film portion (210), and the area of the separable release film portion (220) that overlaps the lower surface of the adhesive sheet portion (110) for application is less than the area of the separable release film portion that does not overlap the adhesive sheet portion (110) for application.

Also, in the medical dressing according to the present invention, a lower support film (300) may be provided under the release film (200).

Also, in the medical dressing according to the present invention, an adhesive layer may be formed at an upper surface of the lower support film (300) such that the release film (200) and the lower support film (300) are fixed to each other.

Also, in the medical dressing according to the present invention, the adhesive sheet portion (110) for application may have larger adhesive force than the adhesive layer of the lower support film (300).

Also, in the medical dressing according to the present invention, the separable release film portion (220) may be constituted by two circular members connected to each other in a state of being spaced apart from each other by a predetermined distance such that a depressed portion (221) is formed therebetween.

In addition, a medical dressing manufacturing method according to the present invention includes a first step of preparing a lower support film (300) having a predetermined thickness, a second step of laminating a release film (200) having a predetermined thickness on the lower support film (300), a third step of shaping the release film (200) so as to be divided into a fixed release film portion (210) and a separable release film portion (220), a fourth step of laminating an adhesive sheet (100) on the release film (200), and a fifth step of shaping the adhesive sheet (100) so as to be divided into an adhesive sheet portion (110) for application and a separable adhesive sheet portion (120).

Also, in the medical dressing manufacturing method according to the present invention, an adhesive layer may be formed on the lower support film (300).

Also, in the medical dressing manufacturing method according to the present invention, the adhesive sheet portion (110) for application may have larger adhesive force than the adhesive layer of the lower support film (300).

Also, the medical dressing manufacturing method according to the present invention may further include a sixth step of removing the separable adhesive sheet portion (120) after the fifth step.

Also, the medical dressing manufacturing method according to the present invention may further include a seventh step of laminating an upper protective film (400) after the sixth step.

Also, in the medical dressing manufacturing method according to the present invention, the upper protective film (400) may have no adhesive layer.

BRIEF DESCRIPTION OF THE DRAWINGS

FIGS. 4A to 4F are a process view illustrating a method of manufacturing a medical dressing according to an embodiment of the present invention.

DETAILED DESCRIPTION OF THE INVENTION

Figure 1:
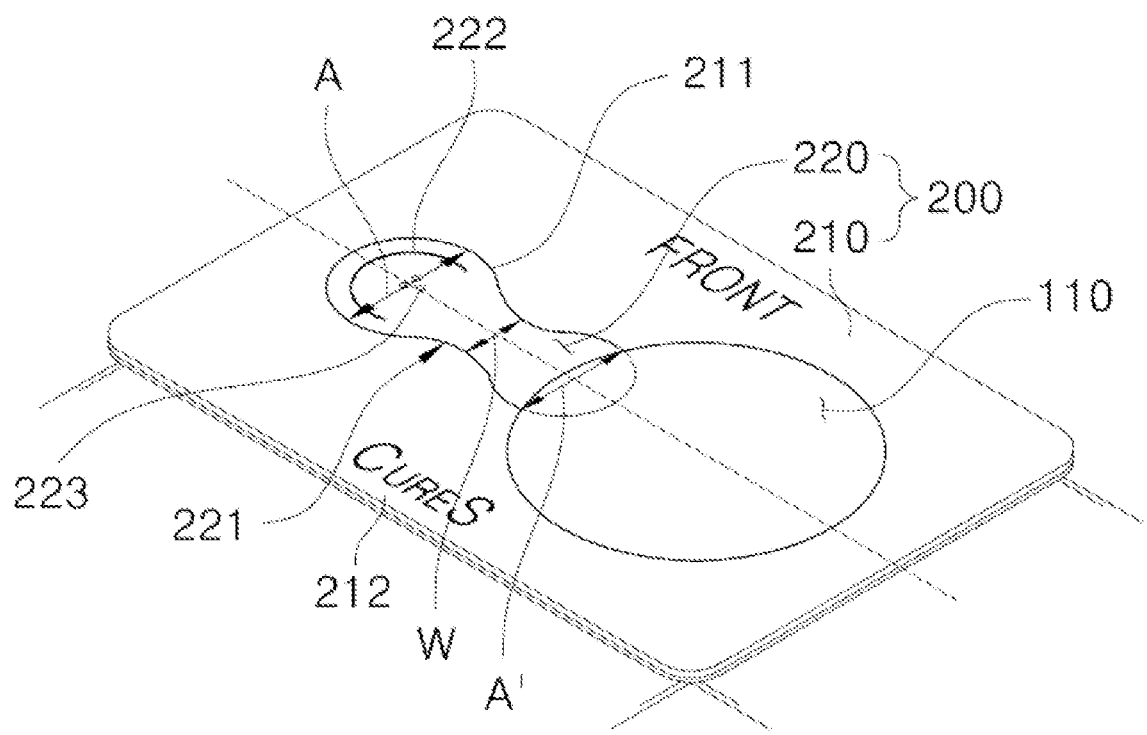
FIG. 1 is a perspective view of a medical dressing according to a first preferred embodiment of the present invention.

In the present application, it should be understood that the terms "comprises," "has," "includes," etc., when used in this specification, specify the presence of stated features, numbers, steps, operations, elements, components, or combinations thereof, but do not preclude the presence or addition of one or more other features, numbers, steps, operations, elements, components, or combinations thereof.

It will be understood that, when a component is referred to as being "connected to" or "coupled to" another component, it may be directly connected to or coupled to the other component, or intervening components may be present. In contrast, when a component is referred to as being "directly connected to" or "directly coupled to" another component, there are no intervening components present. Other terms that describe the relationship between components, such as "between" and "directly between" or "adjacent to" and "directly adjacent to", must be interpreted in the same manner.

Unless otherwise defined, all terms, including technical and scientific terms, used in this specification have the same meanings as those commonly understood by a person having ordinary skill in the art to which the present invention pertains. It will be further understood that terms, such as those defined in commonly used dictionaries, should be interpreted as having meanings consistent with their meanings in the context of the relevant art and the present disclosure, and are not to be interpreted in an idealized or overly formal sense unless expressly so defined herein.

Hereinafter, a medical dressing according to the present invention will be described with reference to the drawings. In the drawings, the same components will be denoted by the same reference numerals, and therefore a duplicate description thereof will be omitted.

Figure 2:
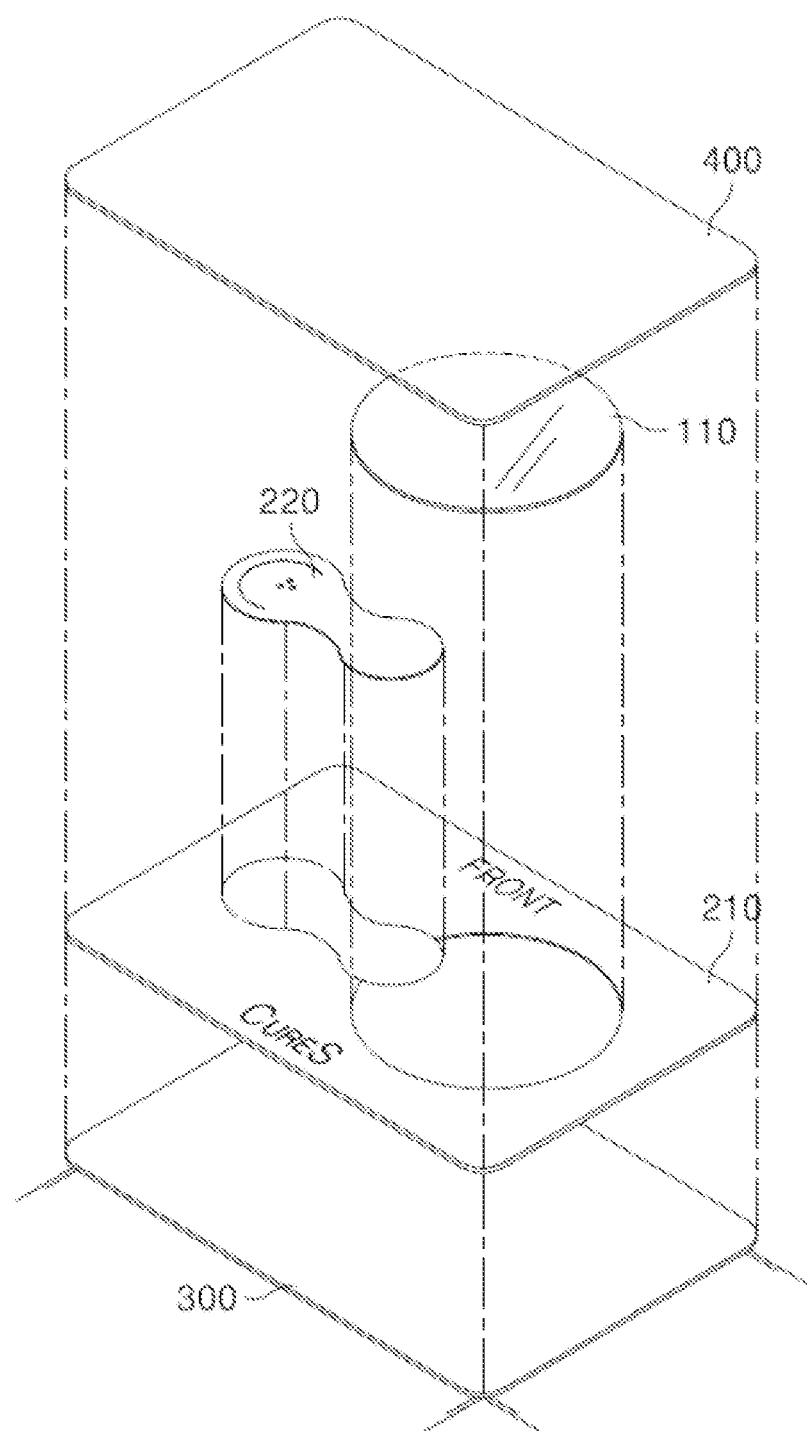
FIG. 2 is an exploded perspective view of the medical dressing shown in FIG. 1.

FIG. 1 is a perspective view of a medical dressing according to a first preferred embodiment of the present invention, and FIG. 2 is an exploded perspective view of the medical dressing shown in FIG. 1.

As shown in FIGS. 1 and 2, the medical dressing according to the first embodiment of the present invention may include an adhesive sheet portion 110 for application, a release film 200, a lower support film 300, and an upper protective film 400.

When describing the release film 200 in detail first, the release film 200 is constituted by a separable release film portion 220 separable along an incision line 211 and a fixed release film portion 210 remaining after the separable release film portion 220 is removed. A smooth coating layer may be formed on at least one surface of each of the fixed release film portion 210 and the separable release film portion 220.

A part of a lower surface of the adhesive sheet portion 110 for application, which is attached to a lesion, is fixed to the separable release film portion 220, and the remainder of the lower surface of the adhesive sheet portion for application is attached to the fixed release film portion 210.

Specifically, the separable release film portion 220 is constituted by two circular members spaced apart from each other by a predetermined distance so as to be easily separable from the fixed release film portion 210, and a depressed portion 221 configured to connect the circular members to each other while having a predetermined radius of curvature may be formed. The width W formed by the depressed portion 221 is less than each of the diameters A and A' of the two circular members. When the separable release film portion 220 is configured to have the above shape, therefore, it is possible to easily hold the large-area circular member by hand. Furthermore, since the depressed portion 221, which has a relatively small width W, is provided, it is possible to smoothly pull the separable release film portion back.

Here, it is preferable for the sectional area of a circular member that does not contact the lower surface of the adhesive sheet portion 110 for application, which is one of the two circular members of the separable release film portion 220, to be greater than the sectional area of a circular member that contacts the lower surface of the adhesive sheet portion for application, which is the other circular member. The reason for this is that it is possible to easily hold the separable release film portion 220 and to easily separate the separable release film portion after the adhesive sheet portion 110 for application is attached to the skin.

In addition, the area of the circular member of the separable release film portion 220 adhered to the adhesive sheet portion 110 for application is preferably 10% to 70%, more preferably 20% to 50%, of the total area of the adhesive sheet portion 110 for application. If the area of the separable release film portion adhered to the adhesive sheet portion 110 for application is less than 10% of the area of the adhesive sheet portion for application, the adhesive force of the separable release film portion 220 is too small, whereby the adhesive sheet portion for application may not be separated when the separable release film portion 220 is separated. If the area of the separable release film portion adhered to the adhesive sheet portion for application is greater than 70% of the area of the adhesive sheet portion for application, on the other hand, the adhesive force of the separable release film portion 220 is too large, whereby the adhesive sheet portion for application may not easily be separated from the adhesive sheet portion 110 for application after the adhesive sheet portion 110 for application is attached to the skin. Consequently, it is preferable for the separable release film portion 220 and the adhesive sheet portion 110 for application to be adhered to each other within the above range.

Furthermore, it is preferable for the central points of the adhesive sheet portion 110 for application and the two circular members constituting the separable release film portion 220 to be located on a virtual extension line. The reason for this is that, when the separable release film portion 220 is separated from the fixed release film portion 210, it is possible to easily separate the adhesive sheet portion 110 for application from the fixed release film portion 210 in a state in which the adhesive sheet portion for application is not twisted or biased to any one side.

Meanwhile, a release film and an adhesive material constituting a recent dressing are very transparent, and therefore it is not possible to easily recognize the surface of the separable release film portion 220 to which the adhesive sheet portion 110 for application is attached in many cases. Particularly, when a user has poor eyesight, such recognition is further difficult. That is, when the separable release film portion 220 is separated in order to use the adhesive sheet portion 110 for application, the separable release film portion 220 must be pulled back in a direction in which the adhesive sheet portion 110 for application is attached in order to separate the separable release film portion 220 in the state in which the adhesive sheet portion 110 for application is attached thereto. If the separable release film portion is pulled back in the opposite direction, only the separable release film portion 220 is separated, whereby it is difficult to use the adhesive sheet portion for application.

In order to remedy such inconvenience in use, it is preferable for a first identification portion 212, a second identification portion 222, and a third identification portion 223 to be provided at the release film 200.

The first identification portion 212, which is provided at a predetermined position of the fixed release film portion 210, may be at least one shape selected from a word, a pattern, and a figure, and the shape may be visually checked, whereby it is possible to easily check the direction in which the adhesive sheet portion 110 for application is attached.

The second identification portion 222, which is provided at the separable release film portion 220, may be at least one shape selected from a pattern, a word, and a figure, similarly to the first identification portion 212. As an example, as shown in FIGS. 1 and 2, the second identification portion may be a belt shape formed along the incision line 211 at a predetermined position of an inner side surface of the separable release film portion 220.

The third identification portion 223, which is provided at the separable release film portion 220, is a portion assisting a user in easily tactilely recognizing the part to be held. As shown in FIGS. 1 and 2, the third identification portion may be at least one protrusion located at a predetermined position of an inner upper part of the separable release film portion 220 adjacent to the incision line 211.

The release film 220, which is constituted by the fixed release film portion 210 and the separable release film portion 220, may be made of a plastic material, such as polyethylene terephthalate (PET) or polyethylene (PE), or various kinds of paper. It is more preferable for the release film to have a thickness of 10 to 300 μm so as to have a predetermined restoring force such that the release film can rapidly return to the original position thereof when curved. If the thickness of the release film is less than 10 μm, which is too small, the restoring force of the release film is insufficient. If the thickness of the release film is greater than 300 μm, the release film is not easily curved, whereby it is not easy to separate the separable release film portion 220. Consequently, it is preferable for the release film 220 to have the above-specified thickness.

The adhesive sheet portion 110 for application, which overlaps a predetermined region of the separable release film portion 220, may be of a hydrocolloid adhesive sheet type or a polyurethane foam adhesive sheet type. The hydrocolloid adhesive sheet is configured such that a hydrophilic hydrocolloid polymer is dispersed on a hydrophobic rubbery matrix attachment surface having adhesive force, and the polyurethane foam adhesive sheet is configured such that a polymer, such as polyethylene glycol, isocyanate, a catalyst, or water, is dispersed in a mixed state on a hydrophobic urethane attachment surface having adhesive force. The hydrocolloid adhesive sheet or the polyurethane foam adhesive sheet, which has wound protection ability resulting from hygroscopicity and moist environment maintenance and excellent adhesive force, is a sheet that is widely used, and therefore a more detailed description thereof will be omitted.

It is preferable for the lower support film 300 to be further provided under the release film 200. When the temperature of the open air is relatively high, viscosity of the adhesive sheet portion 110 for application, which is made of hydrocolloid or polyurethane, may be lowered due to physico-chemical properties thereof, and therefore the adhesive sheet portion for application may flow down through the incision line 211. As a result, a lower surface of the release film 200 sticks to an inner surface of product packaging paper, whereby it is difficult to separate the release film 200 from the packaging paper, which leads to deterioration in marketability. The lower support film 300 is provided to prevent leachate flowing down through the incision line 211 from being attached to the inner surface of the packaging paper.

Furthermore, it is more preferable for an adhesive layer to be provided on an upper surface of the lower support film 300, i.e. the surface of the lower support film that abuts the release film 200.

One of the circular members of the separable release film portion 220 is fixed by the adhesive sheet portion 110 for application in a state of being located under the adhesive sheet portion 110 for application, whereas the other circular member of the separable release film portion is completely separated from the adhesive sheet portion for application, whereby a phenomenon in which the separable release film portion 220 becomes unfastened in the vicinity of the incision line 211 may occur. When the adhesive layer is formed on the upper surface of the lower support film 300, however, it is possible to prevent such a phenomenon.

In particular, since the lower support film 300 is made of a single thin sheet having neither incised portions nor perforated portions, it is possible to most surely check an attachment direction of the separable release film portion 220, and therefore it is possible to completely prevent separation of only the separable release film portion 220.

Here, the lower support film 300 may be made of a plastic material, such as polyethylene terephthalate (PET) or polyethylene (PE), or various kinds of paper. It is preferable for the lower support film 300 to have a thickness of 10 to 300 μm and smaller adhesive force than the adhesive sheet portion 110 for application such that the separable release film portion 220 can be easily separated from the lower support film when being pulled back at a predetermined angle.

If the thickness of the lower support film is less than 10 μm, which is too small, the separable release film portion 220 may not be easily separated. If the thickness of the lower support film is greater than 300 μm, the lower support film is not easily curved, whereby it is not easy to separate the separable release film portion 220. Consequently, it is preferable for the lower support film 300 to have the above-specified thickness.

The upper protective film 400 may be further provided on the release film 200 in order to prevent contamination of the adhesive sheet portion 110 for application. Unlike the lower support film 300, no adhesive layer is provided at the upper protective film 400.

Figure 3:
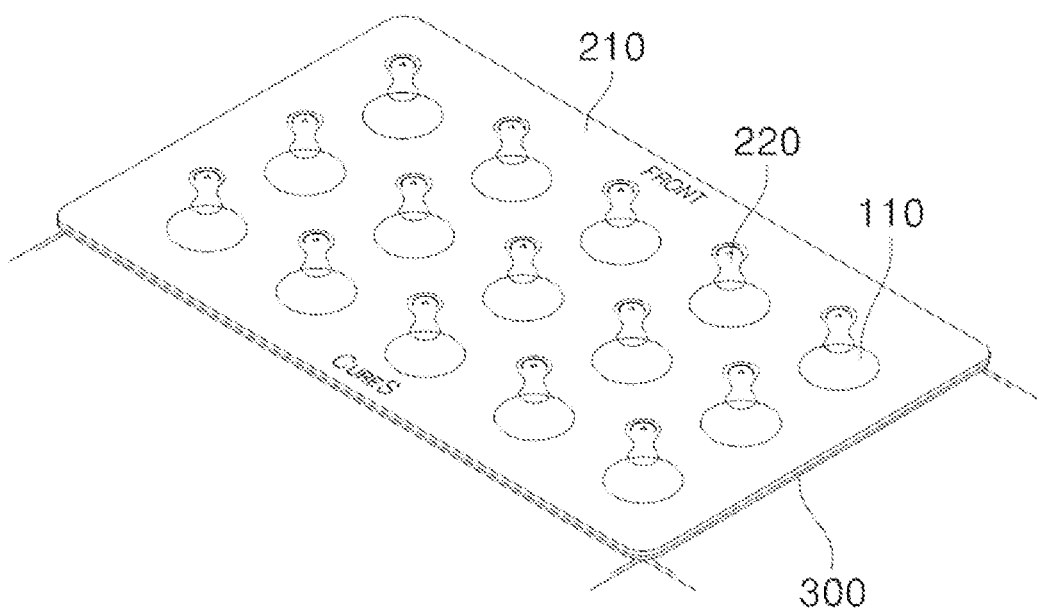
FIG. 3 is a perspective view of a medical dressing according to a second embodiment of the present invention.
Figure 4E:
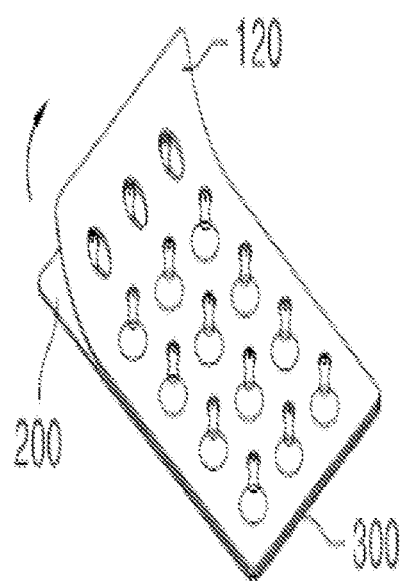
Figure 4F:
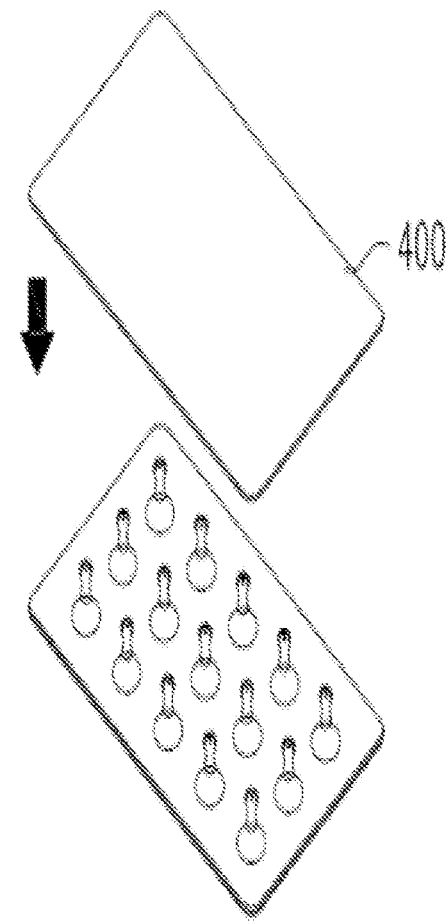

FIG. 3 is a perspective view of a medical dressing according to a second embodiment of the present invention.

The second embodiment of FIG. 3 is identical to the first embodiment described with reference to FIGS. 1 and 2 except for the number and disposition of adhesive sheet portions 110 for application and separable release film portions 220. Accordingly, the same components will be denoted by the same reference numerals, and therefore a duplicate description thereof will be omitted.

In the second embodiment, as shown in FIG. 3, a total of 15 adhesive sheet portions 110 for application arranged in a 3×5 matrix may be provided on an upper surface of one sheet of release film 200 having a predetermined width and area, and a lower support film 300 may be provided on a lower surface of the release film 200.

Here, it is preferable for the separable release film portions 220 to be disposed so as to be inclined at a predetermined angle such that as many adhesive sheet portions 110 for application as possible are attached per unit area of the release film 200. Specifically, when lines on which three adhesive sheet portions 110 for application are arranged are defined as rows and lines on which five adhesive sheet portions 110 for application are arranged are defined as columns, the separable release film portions 220 may be disposed so as to be inclined at an angle of 40 to 50 degrees with respect to the rows or the columns, whereby it is possible to maximize the available area of a fixed release film portion 210.

Hereinafter, a method of manufacturing the medical dressing according to the second embodiment of the present invention (FIG. 3) will be described. FIGS. 4A to 4F are a process view illustrating a method of manufacturing a medical dressing according to an embodiment of the present invention.

The method of manufacturing a medical dressing according to an embodiment of the present invention may include a first step of preparing a lower support film 300 having a predetermined thickness, a second step of laminating a release film 200 having a predetermined thickness on the lower support film 300, a third step of shaping the release film 200 so as to be divided into a fixed release film portion 210 and a separable release film portion 220, a fourth step of laminating an adhesive sheet 100 on the release film 200, a fifth step of shaping the adhesive sheet 100 so as to be divided into an adhesive sheet portion 110 for application and a separable adhesive sheet portion 120, a sixth step of removing the separable adhesive sheet portion 120, and a seventh step of laminating an upper protective film 400.

More specifically, the first step is a step of preparing a lower support film 300 having an adhesive layer of a predetermined thickness formed on one surface thereof. As an example, the lower support film 300 may be configured such that release paper is attached to the surface of the lower support film having the adhesive layer formed thereon in the form of a roll; however, the present invention is not limited thereto.

The second step is a step of laminating a release film 200 on the adhesive layer of the lower support film 300 in the state in which the release paper is removed therefrom, wherein the lower support film 300 and the release film 200 are attached to each other via the adhesive layer. Here, the release film 200 may be provided in the form of a roll; however, the present invention is not limited thereto.

The third step is a step of forming an incision line 211 such that the release film is divided into a fixed release film portion 210 and a separable release film portion 220. As an example, a shaper having a knife edge configured to perform incision in the shape of the separable release film portion 220 may be provided; however, the present invention is not limited thereto.

Conventionally, an adhesive sheet 100 is laminated on the release film 200, and then the separable release film portion 220 is formed by shaping. As a result, an adhesive sheet portion 110 partially overlapping the release film portion 220 may be damaged due to a pressing phenomenon at the time of shaping. In the present invention, however, the separable release film portion 220 is formed by shaping before lamination of the adhesive sheet 100, whereby the adhesive sheet portion 110 is not damaged at all.

Here, it is obvious that the lower support film 300 is not incised even though the incision line is formed in the release film portion 220 in the shape of the separable release film portion 220.

The fourth step is a step of laminating an adhesive sheet 100 on the release film 200. At this time, release paper may be attached to one surface or opposite surfaces of the release film 200 in the form of a roll; however, the present invention is not limited thereto. It is obvious that, in the state in which the release paper is attached, the release paper is removed and then the adhesive sheet is laminated on the release film 200.

The fifth step is a step of shaping the adhesive sheet 100 so as to be divided into an adhesive sheet portion 110 for application and a separable adhesive sheet portion 120. As an example, a shaper having a knife edge configured to perform incision in the shape of the adhesive sheet portion 110 for application may be provided; however, the present invention is not limited thereto.

At this time, in the shaping step, beveling may be simultaneously performed such that a central part of the adhesive sheet portion 110 for application is convex and the periphery of the central part is gently inclined.

The sixth step is a step of removing only the separable adhesive sheet portion 120 in the state in which the adhesive sheet portion 110 for application is left on the release film 200, and the seventh step is a step of laminating an upper protective film 400 on upper surfaces of the release film 200, from which the separable adhesive sheet portion 120 has been removed, and the adhesive sheet portion 110 for application.

Here, a step of cutting the release film 200 to a predetermined size may be further performed between the sixth step and the seventh step, or a step of cutting the release film to a predetermined size may be performed after the seventh step.

Subsequently, a general packaging step is performed. The packaging step may be performed using a known method, and therefore a detailed description thereof will be omitted.

A method of using the medical dressing according to the present invention described above will be described with reference to FIGS. 5 to 7.

Figure 5:
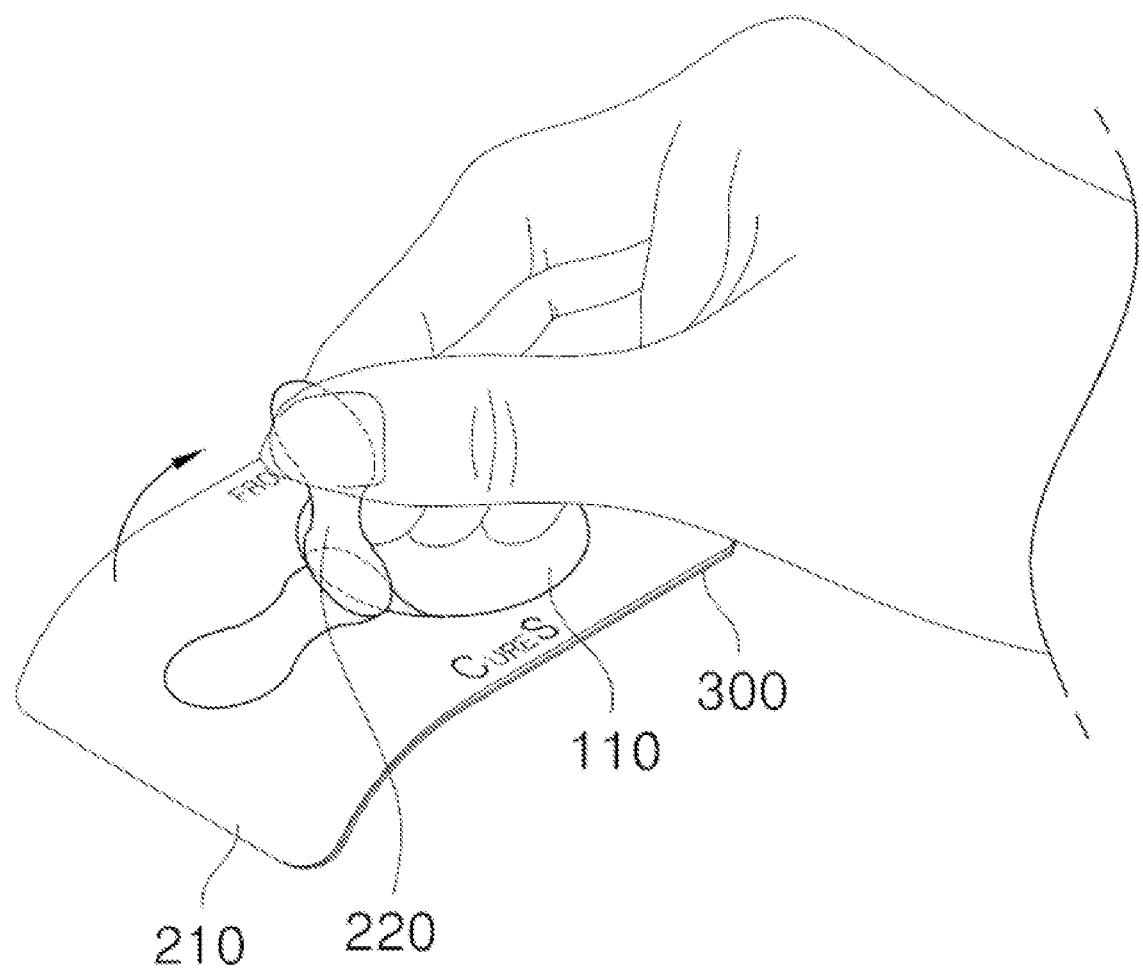
FIGS. 5 and 6 are perspective views illustrating a method of using the medical dressing according to the present invention.
Figure 6:
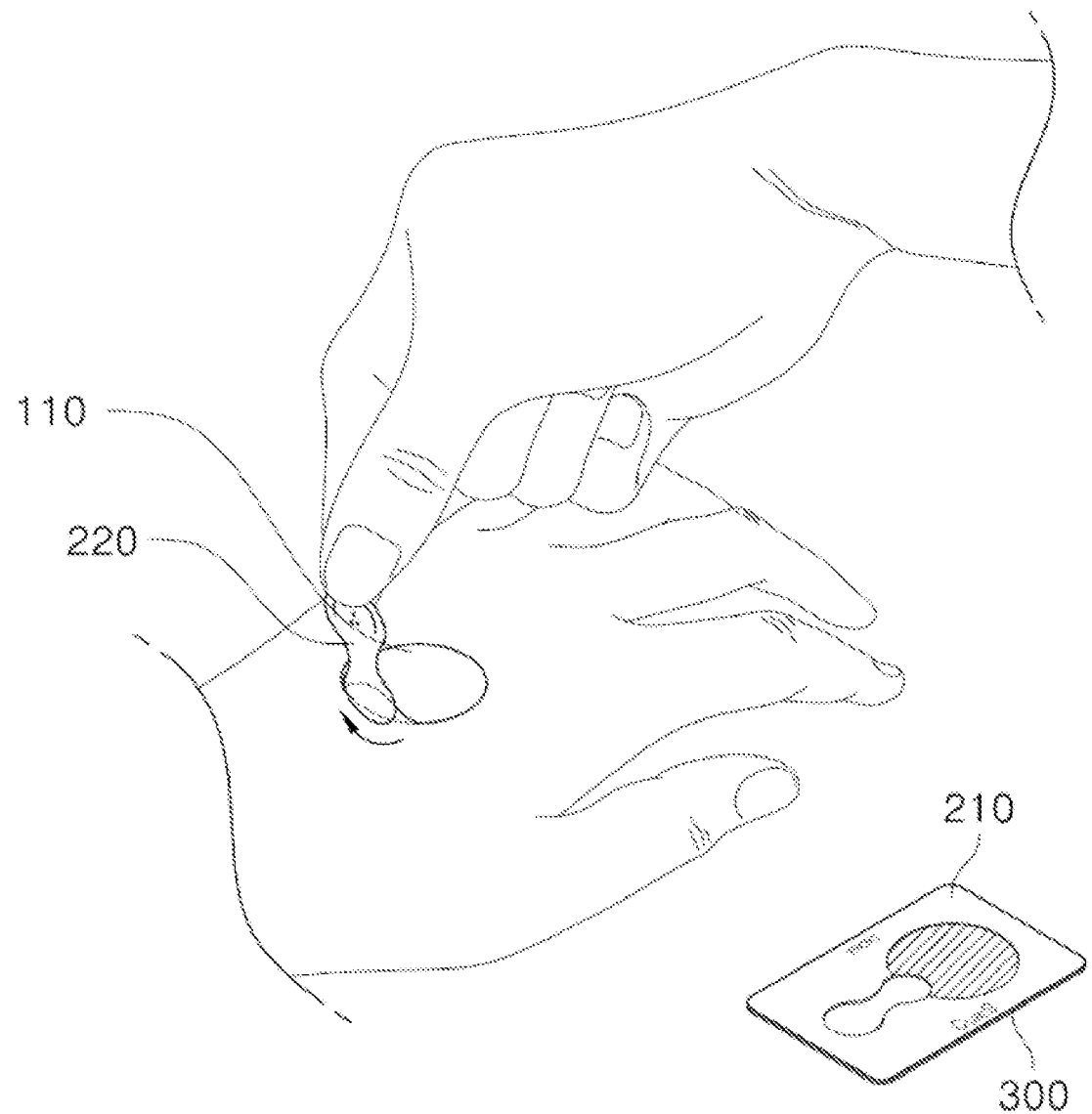
Figure 7:
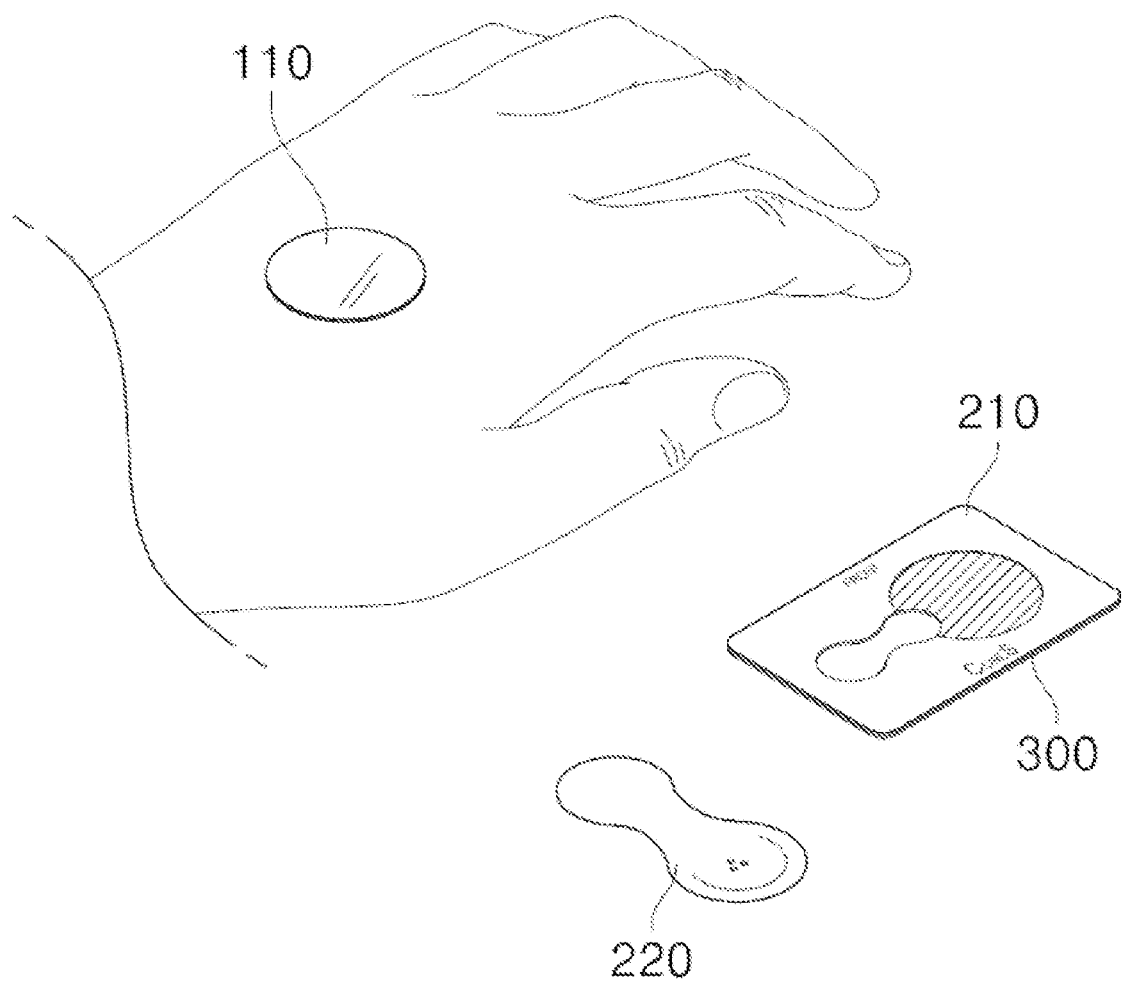
FIG. 7 is a perspective view showing the medical dressing according to the present invention after being used.

FIGS. 5 and 6 are perspective views illustrating a method of using the medical dressing according to the present invention, and FIG. 7 is a perspective view showing the medical dressing according to the present invention after being used.

The fixed release film portion 210, which is adhered to the lower support film 300, is pulled down, and the separable release film portion 220 is separated from the upper surface of the lower support film while a predetermined part of the separable release film portion 220 is held. As a result, the adhesive sheet portion 110 for application, a predetermined part of which is adhered to the separable release film portion 220, is also separated from the lower support film.

Subsequently, the adhesive sheet portion 110 for application is attached to a lesion while the separable release film portion 220 is held, and the separable release film portion 220 is separated from the adhesive sheet portion 110 for application.

Although the specific details of the present invention have been described in detail, those skilled in the art will appreciate that the detailed description thereof discloses only preferred embodiments of the present invention and thus does not limit the scope of the present invention. Accordingly, those skilled in the art will appreciate that various changes and modifications are possible, without departing from the category and the technical idea of the present invention, and it will be obvious that such changes and modifications fall within the scope of the appended claims.

DESCRIPTION OF REFERENCE SYMBOLS

100: Adhesive sheet
110: Adhesive sheet portion for application
120: Separable adhesive sheet portion
200: Release film
210: Fixed release film portion
211: Incision line
212: First identification portion
220: Separable release film portion
221: Depressed portion
222: Second identification portion
223: Third identification portion
300: Lower support film
400: Upper protective film
A, A': Diameters of circular members of separable release film portion
W: Width of depressed portion A medical dressing according to the present invention and a method of manufacturing the same have advantages in that a lower support film having an adhesive layer formed on one surface thereof is laminated under a release film, whereby it is possible to most surely check an attachment direction of a separable release film portion, and therefore it is possible to completely prevent separation of only the separable release film portion, in that it is possible to prevent a phenomenon in which the separable release film portion (220) becomes unfastened in the vicinity of an incision line, and in that the separable release film portion (220) is formed by shaping before lamination of an adhesive sheet (100), whereby an adhesive sheet portion (110) is not damaged at all.

What is claimed is:
1. A medical dressing comprising:
a release film;
an adhesive sheet portion for application located on the release film, the adhesive sheet portion being configured to be attached to a skin; and
a lower support film provided under the release film,
wherein the release film comprises a fixed release film portion and a separable release film portion configured to be separated along an incision line formed in the fixed release film portion,
wherein a predetermined region of the separable release film portion overlaps a lower surface of the adhesive sheet portion for application such that the separable release film portion is separated together with the adhesive sheet portion for application when being separated from the fixed release film portion,
wherein an area of the separable release film portion that overlaps the lower surface of the adhesive sheet portion for application is less than an area of the separable release film portion that does not overlap the adhesive sheet portion for application,
wherein an adhesive layer is formed at an upper surface of the lower support film such that the release film and the lower support film are attached to each other by the adhesive layer,
wherein the adhesive sheet portion for application has larger adhesive force than the adhesive layer of the lower support film.

2. The medical dressing according to claim 1, wherein the separable release film portion has two circular members connected to each other with a depressed portion is formed therebetween.

3. A medical dressing manufacturing method comprising:
  a first step of preparing a lower support film having a predetermined thickness;
  a second step of laminating a release film having a predetermined thickness on the lower support film;
  a third step of shaping the release film to have a shape divided into a fixed release film portion and a separable release film portion;
  a fourth step of laminating an adhesive sheet on the release film; and
  a fifth step of shaping the adhesive sheet to have a shape divided into an adhesive sheet portion for application and a separable adhesive sheet portion,
  wherein an adhesive layer is formed on the lower support film,
  wherein the adhesive sheet portion for application has larger adhesive force than the adhesive layer of the lower support film.

4. The medical dressing manufacturing method according to claim 3, further comprising a sixth step of removing the separable adhesive sheet portion after the fifth step.

5. The medical dressing manufacturing method according to claim 4, further comprising a seventh step of laminating an upper protective film after the sixth step.

6. The medical dressing manufacturing method according to claim 5, wherein the upper protective film has no adhesive layer.

7. A medical dressing comprising:
  a release film;
  an adhesive sheet portion for application located on the release film, the adhesive sheet portion being configured to be attached to a skin; and
  a lower support film provided under the release film,
  wherein the release film comprises a fixed release film portion and a separable release film portion configured to be separated along an incision line formed in the fixed release film portion, wherein the incision line has a closed loop shape,
  wherein a predetermined region of the separable release film portion overlaps a lower surface of the adhesive sheet portion for application such that the separable release film portion is separated together with the adhesive sheet portion for application when being separated from the fixed release film portion,
  wherein an adhesive layer is formed at an upper surface of the lower support film such that the closed-loop shaped separable release film portion of the release film and the adhesive sheet portion are secured at a predetermined position due to the adhesive layer of the lower support film.

8. The medical dressing according to claim 7, wherein an area of the separable release film portion that overlaps the lower surface of the adhesive sheet portion for application is less than an area of the separable release film portion that does not overlap the adhesive sheet portion for application.

9. The medical dressing according to claim 8, wherein the adhesive sheet portion for application has larger adhesive force than the adhesive layer of the lower support film.

10. The medical dressing according to claim 7, wherein the separable release film portion has two circular members connected to each other with a depressed portion formed therebetween.

* * * * *